US008764647B2

(12) United States Patent
Kleyman

(10) Patent No.: US 8,764,647 B2
(45) Date of Patent: Jul. 1, 2014

(54) FOAM PORT DEVICE HAVING CLOSED-END LUMENS

(75) Inventor: Gennady Kleyman, Brooklyn, NY (US)

(73) Assignee: Covidien LP, Mansfield, MA (US)

(*) Notice: Subject to any disclaimer, the term of this patent is extended or adjusted under 35 U.S.C. 154(b) by 361 days.

(21) Appl. No.: 12/938,742

(22) Filed: Nov. 3, 2010

(65) Prior Publication Data

US 2011/0124970 A1     May 26, 2011

Related U.S. Application Data

(60) Provisional application No. 61/263,918, filed on Nov. 24, 2009.

(51) Int. Cl.
*A61B 1/32*      (2006.01)
*A61B 17/34*    (2006.01)

(52) U.S. Cl.
CPC ....... *A61B 17/3423* (2013.01); *A61B 2017/348* (2013.01); *A61B 2017/3488* (2013.01); *A61B 2017/3445* (2013.01); *A61B 2017/3429* (2013.01)
USPC .......................................... 600/208

(58) Field of Classification Search
CPC .................................. A61B 17/3423
USPC ......................... 600/204, 206–208
See application file for complete search history.

(56) References Cited

U.S. PATENT DOCUMENTS

| 4,626,245 | A | * | 12/1986 | Weinstein ............... 604/167.04 |
| 5,336,203 | A | | 8/1994 | Goldhardt et al. |
| 5,366,446 | A | * | 11/1994 | Tal et al. ..................... 604/180 |
| 5,480,410 | A | | 1/1996 | Cuschieri et al. |
| 5,803,921 | A | | 9/1998 | Bonadio |

(Continued)

FOREIGN PATENT DOCUMENTS

| EP | 0807416 B1 | 11/1997 |
| EP | 0950376 | 10/1999 |

(Continued)

OTHER PUBLICATIONS

U.S. Appl. No. 13/091,246, filed Apr. 21, 2011, Paul D. Richard.

(Continued)

*Primary Examiner* — Nicholas Woodall

(57) ABSTRACT

A surgical apparatus includes a seal anchor member. The seal anchor member includes a leading end, a trailing end, and at least one longitudinal port extending between the two ends. The at least one longitudinal port is dimensioned for reception of a surgical object. One end of the at least one longitudinal port is closed by a membrane, which can be pierced through by a sharp-pointed device. The at least one longitudinal port further includes at least one lip therein. The at least one lip is configured to establish a substantially sealed relation with the surgical object entered therethrough, thereby inhibiting the loss of insufflation gas between the at least one longitudinal port and the surgical object.

2 Claims, 6 Drawing Sheets

(56) References Cited

U.S. PATENT DOCUMENTS

| | | | |
|---|---|---|---|
| 5,871,474 A | 2/1999 | Hermann et al. | |
| 5,997,515 A | 12/1999 | de la Torre et al. | |
| 6,162,196 A | 12/2000 | Hart et al. | |
| 6,551,270 B1 | 4/2003 | Bimbo et al. | |
| 6,913,609 B2 | 7/2005 | Yencho et al. | |
| 7,033,319 B2 * | 4/2006 | Pulford et al. | 600/208 |
| 7,101,353 B2 | 9/2006 | Lui et al. | |
| 7,481,765 B2 | 1/2009 | Ewers et al. | |
| 7,798,898 B2 | 9/2010 | Luciano, Jr. et al. | |
| 7,837,612 B2 | 11/2010 | Gill et al. | |
| 8,038,652 B2 | 10/2011 | Morrison et al. | |
| 8,273,017 B1 * | 9/2012 | Moreno | 600/208 |
| 2005/0148823 A1 | 7/2005 | Vaugh et al. | |
| 2005/0277946 A1 | 12/2005 | Greenhalgh | |
| 2006/0129165 A1 | 6/2006 | Edoga et al. | |
| 2006/0161050 A1 | 7/2006 | Butler et al. | |
| 2006/0212063 A1 | 9/2006 | Wilk | |
| 2006/0247498 A1 | 11/2006 | Bonadio et al. | |
| 2006/0247499 A1 | 11/2006 | Butler et al. | |
| 2006/0247500 A1 | 11/2006 | Voegele et al. | |
| 2006/0247516 A1 | 11/2006 | Hess et al. | |
| 2006/0247586 A1 | 11/2006 | Voegele et al. | |
| 2006/0247673 A1 | 11/2006 | Voegele et al. | |
| 2006/0247678 A1 | 11/2006 | Weisenburgh, II et al. | |
| 2006/0270911 A1 | 11/2006 | Voegele et al. | |
| 2009/0036745 A1 | 2/2009 | Bonadio et al. | |
| 2009/0093752 A1 | 4/2009 | Richard et al. | |
| 2009/0093850 A1 | 4/2009 | Richard | |
| 2009/0131751 A1 | 5/2009 | Spivey et al. | |
| 2009/0187079 A1 | 7/2009 | Albrecht et al. | |
| 2009/0227843 A1 | 9/2009 | Smith et al. | |
| 2009/0326332 A1 | 12/2009 | Carter | |
| 2010/0240960 A1 | 9/2010 | Richard | |
| 2010/0286484 A1 | 11/2010 | Stellon et al. | |
| 2011/0034778 A1 | 2/2011 | Kleyman | |

FOREIGN PATENT DOCUMENTS

| | | |
|---|---|---|
| EP | 1 774 918 A1 | 4/2007 |
| EP | 2044889 A1 | 4/2009 |
| EP | 2044897 A1 | 4/2009 |
| EP | 2098182 A2 | 9/2009 |
| EP | 2248478 A1 | 11/2010 |
| WO | WO 97/33520 | 9/1997 |
| WO | WO 99/16368 | 4/1999 |
| WO | WO 01/49363 A1 | 7/2001 |
| WO | WO 2006/110733 A2 | 10/2006 |
| WO | WO 2008/042005 | 4/2008 |
| WO | WO 2008/093313 A1 | 8/2008 |
| WO | WO 2008/121294 A1 | 10/2008 |

OTHER PUBLICATIONS

U.S. Appl. No. 13/031,352, filed Feb. 21, 2011, Gennady Kleyman.
U.S. Appl. No. 13/193,647, filed Jul. 29, 2011, Russell Pribanic.
U.S. Appl. No. 13/217,717, filed Aug. 25, 2011, Joshua Stopek.
U.S. Appl. No. 13/221,062, filed Aug. 30, 2011, Gregory Okoniewski.
U.S. Appl. No. 13/223,029, filed Sep. 1, 2011, Michael Davis.
U.S. Appl. No. 13/223,330, filed Sep. 1, 2011, Gregory Okoniewski.
U.S. Appl. No. 13/223,336, filed Sep. 1, 2011, Michael Davis.
U.S. Appl. No. 13/223,613, filed Sep. 1, 2011, Greg Fischvogt.
U.S. Appl. No. 13/223,627, filed Sep. 1, 2011, Gregory Okoniewski.
U.S. Appl. No. 13/223,645, filed Sep. 1, 2011, Gennady Kleyman.
U.S. Appl. No. 13/223,659, filed Sep. 2, 2011, Francesco Alfieri.
U.S. Appl. No. 13/223,678, filed Sep. 1, 2011, Gregory Okoniewski.
U.S. Appl. No. 13/223,700, filed Sep. 1, 2011, Gennady Kleyman.
U.S. Appl. No. 13/224,353, filed Sep. 2, 2011, Gennady Kleyman.
U.S. Appl. No. 13/224,354, filed Sep. 2, 2011, Greg Okoniewski.
U.S. Appl. No. 13/224,355, filed Sep. 2, 2011, Anibal Rodrigues Jr.
U.S. Appl. No. 13/224,358, filed Sep. 2, 2011, Andrew Barnes.
U.S. Appl. No. 13/228,937, filed Sep. 9, 2011, Dino Kasvikis.
U.S. Appl. No. 13/228,960, filed Sep. 9, 2011, Russell Pribanic.
European Search Report EP08253236 dated Feb. 10, 2009.
European Search Report EP09251613 dated Mar. 24, 2011.
European Search Report EP10250526 dated Jun. 23, 2010.
European Search Report EP10250638 dated Jul. 19, 2010.
European Search Report EP10250643 dated Jun. 23, 2010.
European Search Report EP10250881 dated Aug. 18, 2010.
European Search Report EP10250885 dated Aug. 18, 2010.
European Search Report EP10250944 dated Jul. 29, 2010.
European Search Report EP10251218 dated Jun. 15, 2011.
European Search Report EP10251317 dated Oct. 15, 2011.
European Search Report EP10251359 dated Nov. 8, 2010.
European Search Report EP10251399 dated Sep. 13, 2010.
European Search Report EP10251486 dated Oct. 19, 2010.
European Search Report EP10251693 dated Feb. 3, 2011.
European Search Report EP10251718 dated Jan. 28, 2011.
European Search Report EP10251751 dated Apr. 28, 2011.
European Search Report EP10251796 dated Jan. 31, 2011.
European Search Report EP10251955 dated Feb. 21, 2011.
European Search Report EP10251983 dated Feb. 15, 2011.
European Search Report EP10251985 dated Feb. 15, 2011.
European Search Report EP10251986 dated Mar. 7, 2011.
European Search Report for corresponding EP 10251984 date of mailing is Feb. 18, 2011 (3 pages).

* cited by examiner

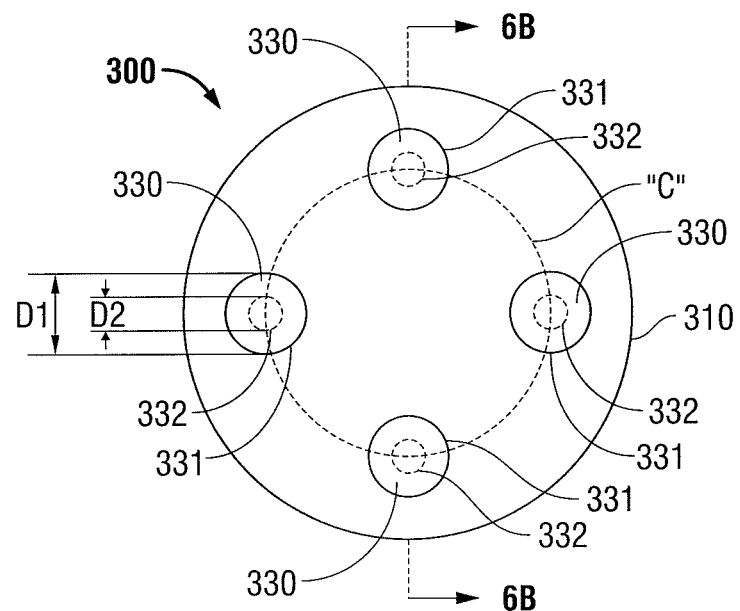
FIG. 6A
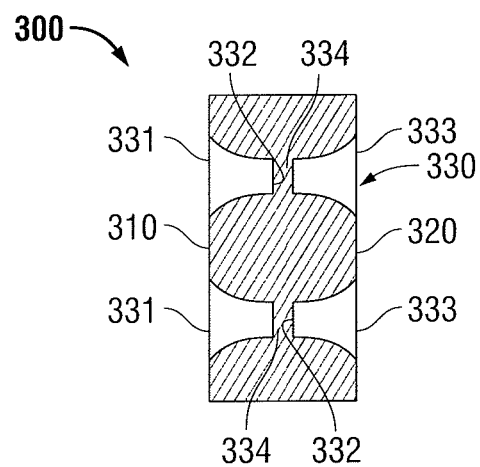
FIG. 6B1
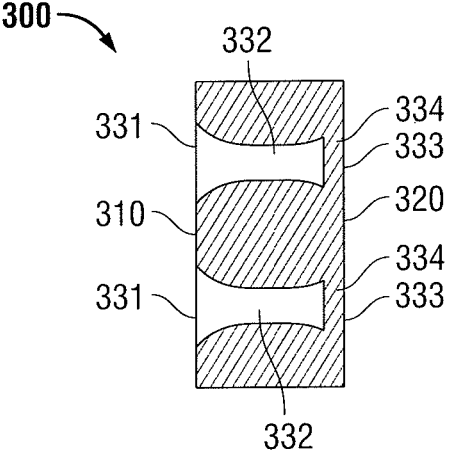
FIG. 6B2

FOAM PORT DEVICE HAVING CLOSED-END LUMENS

CROSS-REFERENCE TO RELATED APPLICATIONS

The present application claims priority to, and the benefit of, U.S. Provisional Application Ser. No. 61/263,918 filed Nov. 24, 2009, the entire contents of which are hereby incorporated by reference.

BACKGROUND

1. Technical Field

The present disclosure relates generally to surgical portals for use in minimally invasive surgical procedures, such as endoscopic and/or laparoscopic procedures, and more particularly, relates to a surgical portal that allows multiple surgical instruments to be inserted through a single incision.

2. Description of Related Art

Today, many surgical procedures are performed through small incisions in the skin, as compared to the larger incisions typically required in traditional procedures, in an effort to reduce both trauma to the patient and recovery time. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures.

During a typical minimally invasive procedure, surgical objects, such as endoscopes, graspers, staplers, or forceps, are inserted into the patient's body through the incision in tissue. In general, prior to the introduction of the surgical object into the patient's body, insufflation gas is used to enlarge the area surrounding the target surgical site to create a larger, more accessible work area. Accordingly, the maintenance of a substantially fluid-tight seal is desirable so as to inhibit the escape of the insufflation gas and the deflation or collapse of the enlarged surgical site.

To this end, various access devices with sealing features are used during the course of minimally invasive procedures to inhibit the escape of the insufflation gas as well as to provide an access for surgical objects to enter the patient's body. Generally, an access device is made of resilient material and has a plurality of ports, and each port is designed to accommodate one surgical object to be inserted therethrough. In the prior art, each port is designed to have a diameter smaller than that of the surgical object uniformly throughout the length of the port. When a surgical object advances through a port, the resilient material is adapted to frictionally engage the surgical object, thus forming a seal between the surgical object and the port along the length of the port. However, because the surgical object is relatively larger in size in comparison to the port, and also because of the friction at the contact surfaces between the surgical object and the port, a large amount of efforts need to be made in order to push or pull the surgical object through the port.

Further, in the prior art, each port is open-ended. Therefore, before the insertion of surgical objects through the open-ended ports of the access device, the insufflation gas may escape from the patient's cavity body through the open-ended ports. For the same reason, foreign matter may inadvertently enter into the patient's cavity body through the open-ended ports. To overcome this problem, cannula assemblies have been used heretofore to couple with the prior access devices together providing a sealed passage for the surgical objects to access the patient's body. A cannula is a tubular member that is positioned within the prior access device through the port, providing a passage for a surgical object to access the patient's body. Typically, the cannula includes respective proximal and distal ends, an elongate member disposed therebetween, and a seal housing positioned at the proximal end. The elongate member defines an opening dimensioned to permit the passage of surgical object. Further, the elongate member is longer in length than that of the open-ended port. Thus, upon positioning, the distal end of the elongate member of the cannula reaches beyond the distal end of the open-ended port and extends into the patient's body cavity. Furthermore, the seal housing of the cannula is adapted to receive the surgical object inserted through the elongate member so as to form a substantially fluid-tight seal with the surgical object. Because the diameter of the seal housing is substantially larger than the diameter of the open-ended port, the seal housing is thus inhibited from entering the open-ended port. Therefore, upon positioning, the seal housing is positioned outside the access device, i.e. positioned above the opening of the open-ended port. Further, the cannula includes a closure valve which is normally closed in the absence of a surgical object. The closure valve thus inhibits gas leakage and introduction of foreign matter in its closed state, therefore serving as a complement to the open-ended ports.

In the prior art, during the operation of the access device, a surgeon introduces the access device into the incision either before or after introducing insufflation gas into the surgical site. After placing the prior access device into the incision and before inserting surgical objects therethrough, the surgeon inserts a cannula into each open-ended port of the access device. When multiple cannulas are positioned within the access device concurrently, the seal housings of the cannulas are all positioned above the access device. The seal housings may clash against each other as the surgeon manipulates multiple surgical objects that are inserted through the multiple cannulas simultaneously. The collisions among the seal housings not only cause great interference with the movements of the surgical objects, but also limit the number of cannulas that can coexist within an access device of a given size, thereby reducing the number of surgical objects that can simultaneously operate through the access device. Similarly, the distal ends of the cannulas, which are positioned inside the patient's body cavity, may also cause interference with the instrument motion, as the distal ends of the cannulas clash within the body cavity. Further, in the prior art, the surgical objects that are inserted through a single access port via cannulas have a limited freedom of movement constrained by the physical characteristics of the cannulas and the open-ended ports. For instance, an open-ended port provides an open channel in a longitudinal direction of the access port. For that reason, the elongate member of the cannula, when positioned within the open-ended port, provides a channel for the surgical objects to maneuver in a longitudinal direction relative to the access port. However, to reach a desired operation site within the patient's body cavity, the surgeon often needs to move the surgical object in a slanting or sloping direction relative to the access port.

Thus, to facilitate and provide greater freedom of movement of the surgical objects and to avoid potential interferences therewith, a continuing need exists for an access device with enhanced sealing features and enhanced port features.

SUMMARY

The present disclosure pertains to a surgical apparatus that includes a seal anchor member. The seal anchor member includes a leading end, a trailing end, and at least one longitudinal port extending between the two ends. The at least one longitudinal port is dimensioned for the reception of a surgical object.

In one embodiment of the seal anchor member, the at least one longitudinal port includes at least one lip therein. The at least one lip is configured to establish a substantially sealed relation with the surgical object inserted therein, thereby inhibiting the loss of insufflation gas between the at least one longitudinal port and the surgical object.

In another embodiment of the seal anchor member, the at least one longitudinal port has an hourglass configuration.

In a certain embodiment, the at least one longitudinal port is closed by a membrane that can be located anywhere along the length of the port.

In some embodiments, the seal anchor member as a whole exhibits an hourglass configuration.

In alternate embodiments, the seal anchor member as a whole exhibits a disk-like configuration.

In a certain embodiment, the seal anchor member comprises a plurality of ports. The ports are substantially parallel to the longitudinal axis of the seal anchor member.

Further, the seal anchor member comprises a port configured to provide a passage for introducing insufflation fluids to the underlying peritoneal cavity of the patient and evacuating fluids from the underlying peritoneal cavity.

DESCRIPTION OF THE DRAWINGS

The above and other aspects, features, and advantages of the present disclosure will become more apparent in light of the following detailed description when taken in conjunction with the accompanying drawings in which:

FIG. 6A is a top perspective view of another alternate embodiment of the surgical apparatus of FIG. 1;

FIG. 6B1 is an end cross-sectional view of the surgical apparatus of FIG. 6A take along the line 6B-6B; and FIG. 6B2 is an end cross-sectional view of an alternate embodiment of the surgical apparatus of FIG. 6A taken along the line 6B-6B.

DETAILED DESCRIPTION

Figure 1:
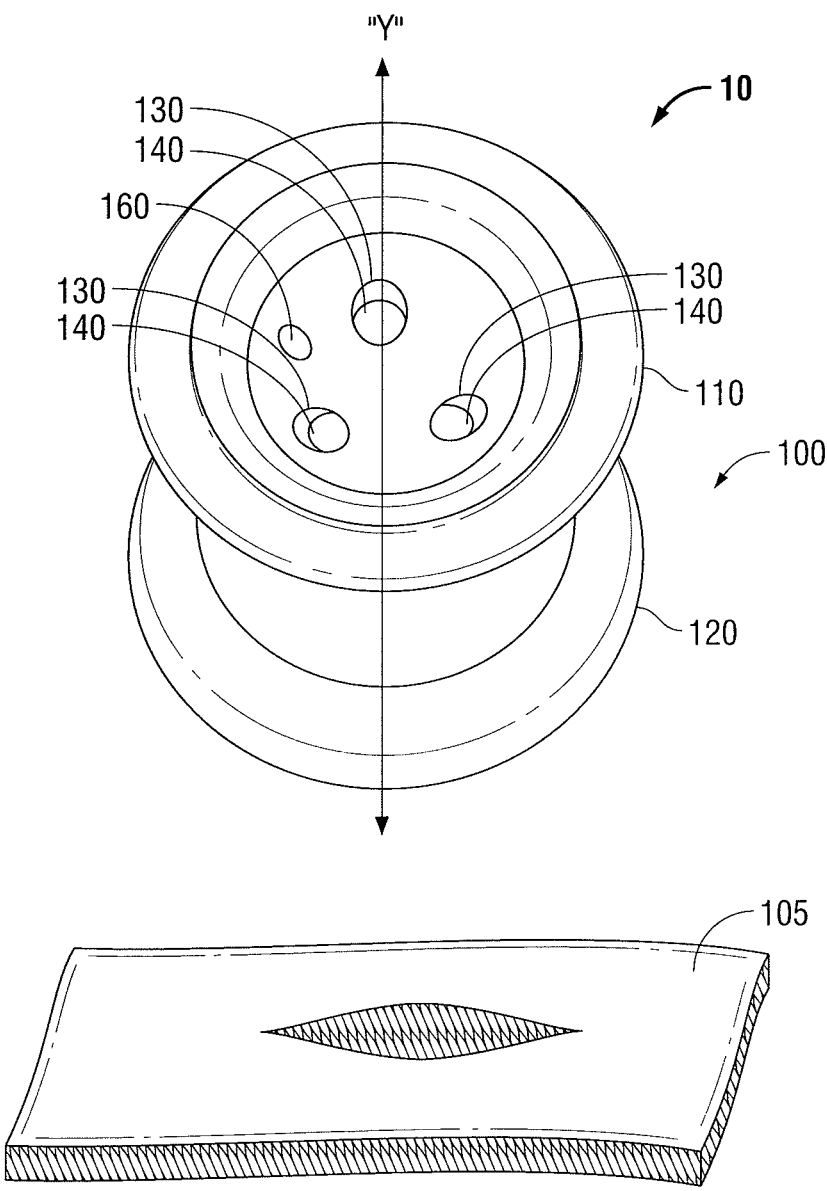
FIG. 1 is a perspective view of a surgical apparatus in accordance with the principles of the present disclosure.

Particular embodiments of the present disclosure will be described herein with reference to the accompanying drawings. As shown in the drawings and as described throughout the following description, and as is traditional when referring to relative positioning on an object, the term "proximal" or "trailing" refers to the end of the apparatus that is closer to the user and the term "distal" or "leading" refers to the end of the apparatus that is farther from the user. In the following description, well-known functions or constructions are not described in detail to avoid obscuring the present disclosure in unnecessary detail.

One type of minimal invasive surgery described herein employs a device that facilitates multiple instrument access through a single incision. This is a minimally invasive surgical procedure, which permits a surgeon to operate through a single entry point, typically the patient's navel. Additionally, the presently disclosed device may be used in a procedure where a naturally occurring orifice (e.g. vagina or anus) is the point of entry to the surgical site. The disclosed procedure involves insufflating the peritoneal cavity and positioning a portal member within, e.g., the navel of the patient. Instruments including an endoscope and additional instruments such as graspers, staplers, forceps or the like may be introduced within the portal member to carry out the surgical procedure. An example of such a surgical portal is disclosed in commonly assigned U.S. patent application Ser. No. 12/244,024, US Pub. No. 2009/0093752 A1, filed Oct. 2, 2008, the entire contents of which are hereby incorporated by reference herein.

Referring now to the drawings, in which like reference numerals identify identical or substantially similar parts throughout the several views, FIG. 1 illustrates a surgical apparatus 10 including a seal anchor member 100 which is adapted for insertion within a tissue tract 105, e.g., through the abdominal or peritoneal lining in connection with a laparoscopic surgical procedure.

With continued reference to FIG. 1, the seal anchor member 100 has a trailing end 110, and a leading end 120. The seal anchor member 100 further comprises at least one longitudinal port 130 extending in a direction substantially parallel to a longitudinal axis "Y" of the seal anchor member 100 between its trailing end 110 and its leading end 120. Each longitudinal port 130 defines a passage extending between the trailing end 110 and the leading end 120. Each passage is dimensioned for receiving a surgical object, e.g. a surgical instrument (not shown) therethrough. Seal anchor member 100 may define an hourglass shape as shown, or may define any other shape, such as a disk-like shape as described later. Trailing and leading ends 110, 120 may define flange segments, which may be integrally formed with seal anchor member 100. Seal anchor member 100 may be made from a resilient, disposable, compressible, and/or flexible type material, for example, but not limited to, a suitable foam, gel material, or soft rubber having sufficient compliance to form a seal about one or more surgical objects, and also establish a sealing relation with tissue. The foam is preferably sufficiently compliant to accommodate off axis motion of the surgical object. In one embodiment, the foam includes a polyisoprene material.

Figure 2:
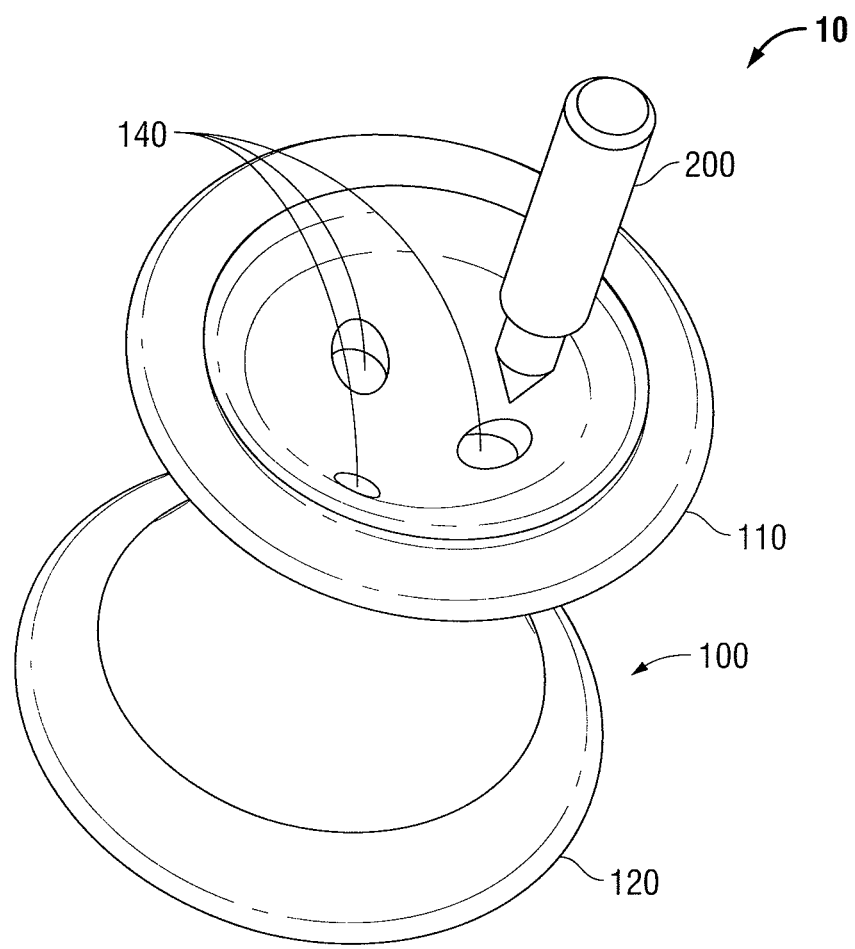
FIG. 2 is a perspective view of the surgical apparatus with a sharp-pointed device placed above one of the ports of FIG. 1.

With reference to FIGS. 1 and 2, each of the longitudinal ports 130 has a membrane 140 disposed within the passage thereof to close one end of the passage. More specifically, as illustrated in FIG. 2, the membranes 140 are disposed within the passages of the longitudinal ports 130 at the trailing end 110 thereof. It should be recognized that, in other embodiments, the membranes 140 may be disposed at the leading end 120 of the longitudinal ports 130, or at any position between the trailing 110 and leading 120 ends. The membrane 140 is made of a gas-impermeable, liquid-impermeable material that prevents passage of gases and liquids. During a minimally invasive procedure, after seal anchor member 100 is inserted within a tissue tract 105, the membranes 140 serve the purpose of closing the longitudinal ports 130, thereby inhibiting the escape of the insufflation gas from the patient's peritoneal cavity, and thus inhibiting the deflation or collapse of the enlarged surgical site. The membranes 140, by closing the longitudinal ports 130, also inhibit foreign matter from inadvertently entering into the patient's peritoneal cavity. Further, the material that the membranes 140 are made of has a property that allows easy penetration therethrough by a sharp-pointed object. As illustrated in FIG. 2, after placing the seal anchor member 100 into the tissue tract and before inserting surgical instruments therethrough, a sharp-pointed device, such as a cylindrical knife 200, is used to cut open the membranes 140 by piercing through the membranes 140 from the trailing end 110.

Figure 3:
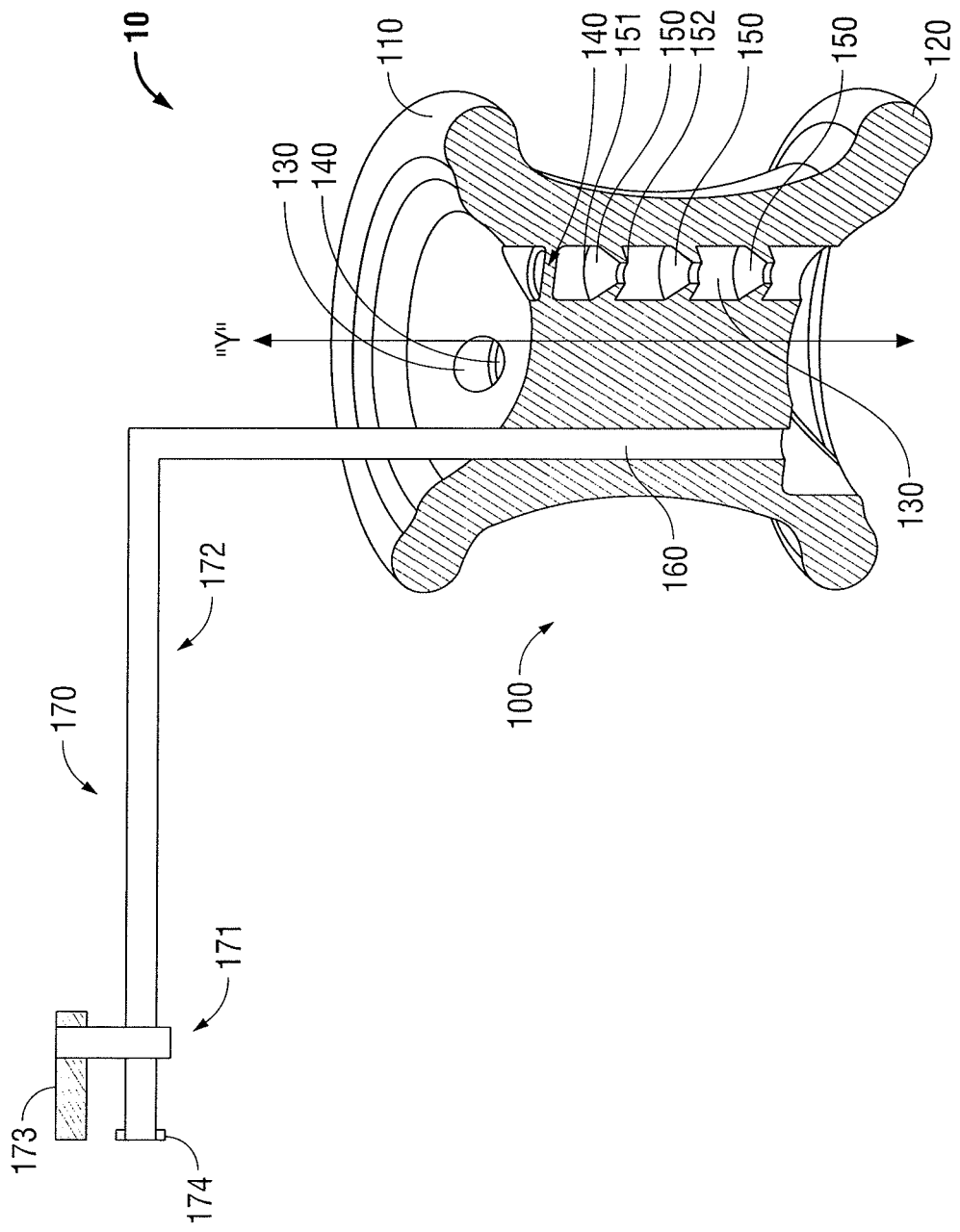
FIG. 3 is a side cross-sectional view of the surgical apparatus illustrating a plurality of lips placed through one of the ports of FIG. 1 and an insufflation/evacuation implement.

With reference to FIG. 3, each of the longitudinal ports 130 further comprises at least one lip 150. Lips 150 are positioned throughout each longitudinal port 130 in parallel to the longitudinal axis "Y" of the seal anchor member 100. Lips 150 are designed to seal surgical instruments during minimally invasive procedures. In one embodiment as illustrated in FIG. 3, each lip 150 may exhibit a conical, or frustoconical shape. Each conical shape has a round base end 151 which has the same diameter as that of the longitudinal ports 130, and a round apex end 152 having a diameter substantially smaller than that of the round base 151. As the surgical instrument enters the longitudinal port 130, the surgical instrument advances through each lip 150. Further, the diameter of the longitudinal ports 130 is designed larger in size than that of the surgical instruments, and the diameter of the round apex end 152 is smaller than that of the surgical instruments. Due to the resilient nature of the material that the seal anchor member 100 is made of, as the surgical instrument advances through each lip 150, the apex end 152 of each lip 150 is forced to expand to permit passage of the surgical instrument. Further, the apex end 152 in its expanded state forms a substantially tight seal with the surgical instrument, thus establishing a substantially sealed relation with the surgical instrument. As the surgical instrument leaves each lip 150 upon removal, the apex end 152 contracts back to its original shape.

The current disclosure obviates the need for discrete cannula assemblies. Specifically, due to the membranes 140 of the seal anchor member 100 of the present disclosure, the seal anchor member 100 of the present disclosure does not require a separate cannula assembly to be inserted into each longitudinal port 130 to inhibit insufflation gas leakage. Additionally, due to the lips 150 of the seal anchor member 100 of the present disclosure which form tight seals with surgical instruments passed therethrough, gas leakage through the longitudinal ports 130 can be minimized or eliminated in the absence of cannula assemblies inserted therein.

Further, the seal anchor member 100 provides a substantially increased ease of use during operations. Here, the surgical instrument experiences friction only when it advances through the round apex end 152 of each lip 150 within the seal anchor member 100, as opposed to experiencing friction throughout the entire length of the ports as in prior art devices. Thus, in use, introducing or removing the surgical instrument into or from the port requires less force than in the prior art ports.

It is contemplated that the port 130 may include a seal, disposed within the port 130, that is biased into a closed position, and adapted to open upon the introduction of the surgical instrument inserted into the port 130 and allow the surgical instrument to pass therethrough. In the closed position, i.e., in the absence of surgical instrument, the seal inhibits the communication of insufflation gas or foreign matter therethrough.

Further, due to its very compliant nature, the seal anchor member 100 is adapted to accommodate surgical instruments of various shapes, such as curved surgical instruments. During insertion of a surgical instrument into the seal anchor member 100, the seal anchor member 100 can immediately conform to the shape of the surgical instrument. Thus, no particular shape is required for the surgical instrument.

As illustrated in FIG. 3, the longitudinal ports 130 are substantially parallel to the longitudinal axis "Y" of the seal anchor member 100. The ports 130 are configured symmetrically with respect to the longitudinal axis "Y". The ports 130 are spaced equidistant from the longitudinal axis "Y". Each port 130 is spaced equidistant from its neighboring ports. Of course, it should be recognized that the longitudinal ports 130 may be non-parallel relative to the longitudinal axis "Y", may be arranged asymmetrically with respect to the longitudinal axis "Y", and/or may be spaced at varying distances from the longitudinal axis "Y" and from each other.

Figure 4:
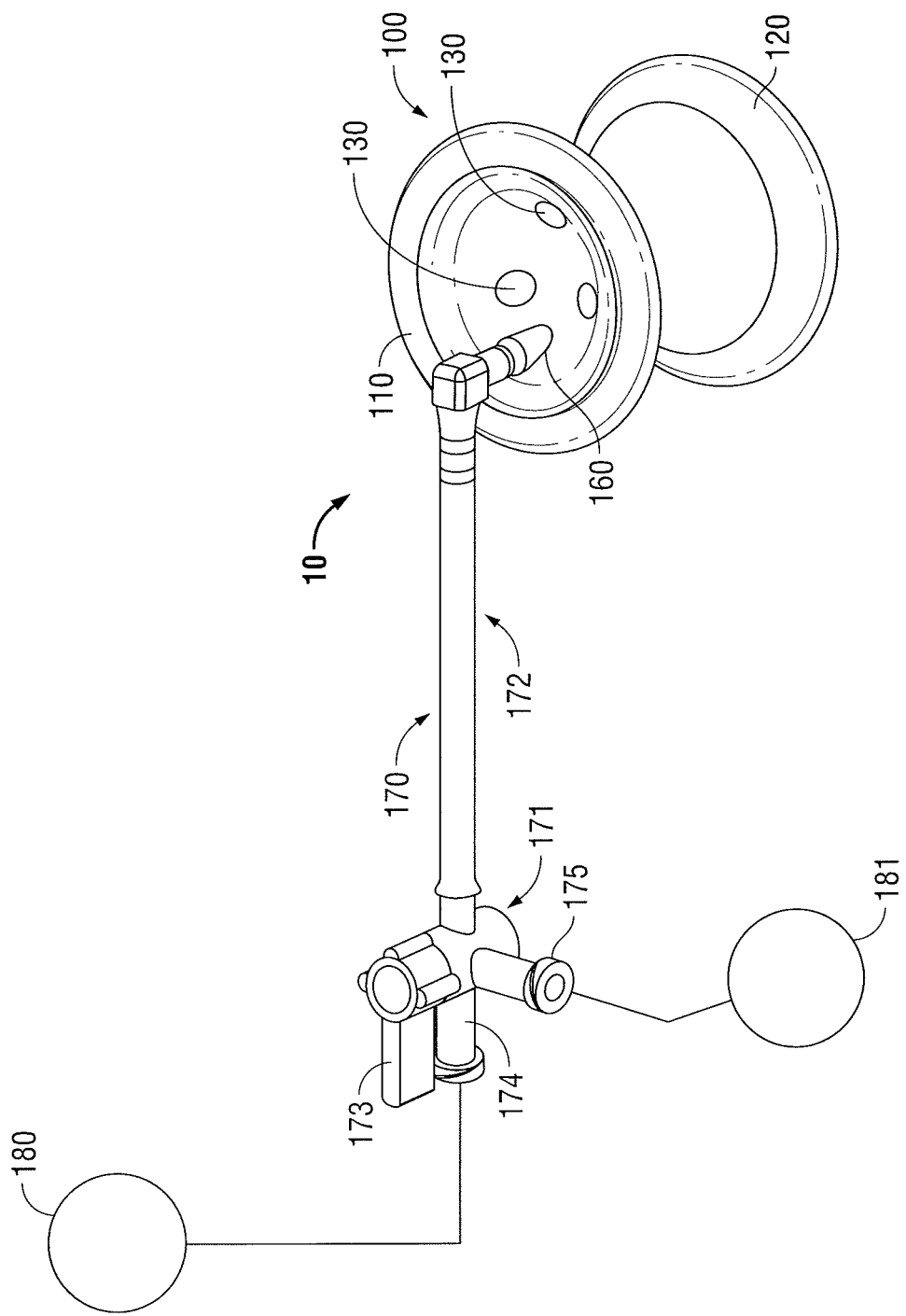
FIG. 4 illustrates the surgical apparatus and the insufflation/evacuation implement of FIG. 3.

In one embodiment, as illustrated in FIGS. 3 and 4, seal anchor member 100 further comprises a port 160 which serves as a fluid delivery channel. The port 160 connects with an insufflation/evacuation instrument 170. The insufflation/evacuation instrument 170 may be any suitable instrument adapted to convey fluids or introduce insufflation fluids, e.g., $CO_2$ into the peritoneal cavity, and/or evacuate smoke or fluids from the cavity. The insufflation/evacuation instrument 170 includes housing 171 and elongated member 172 extending from the housing. Housing 171 incorporates a stop cock valve 173 to permit selective passage and interruption of fluids. As shown in FIG. 4, housing 171 includes first and second ports or luer connectors 174, 175 adjacent to stop cock valve 173. First luer connector 174 may be adapted for connection to an insufflation source 180 such as $CO_2$ utilized to insufflate the peritoneal cavity. Second luer connector 175 may be adapted for fluid connection to an aspiration or gas evacuator 181. Elongated member 172 defines a fluid conduit in communication with stop cock valve 173.

Figure 5A:
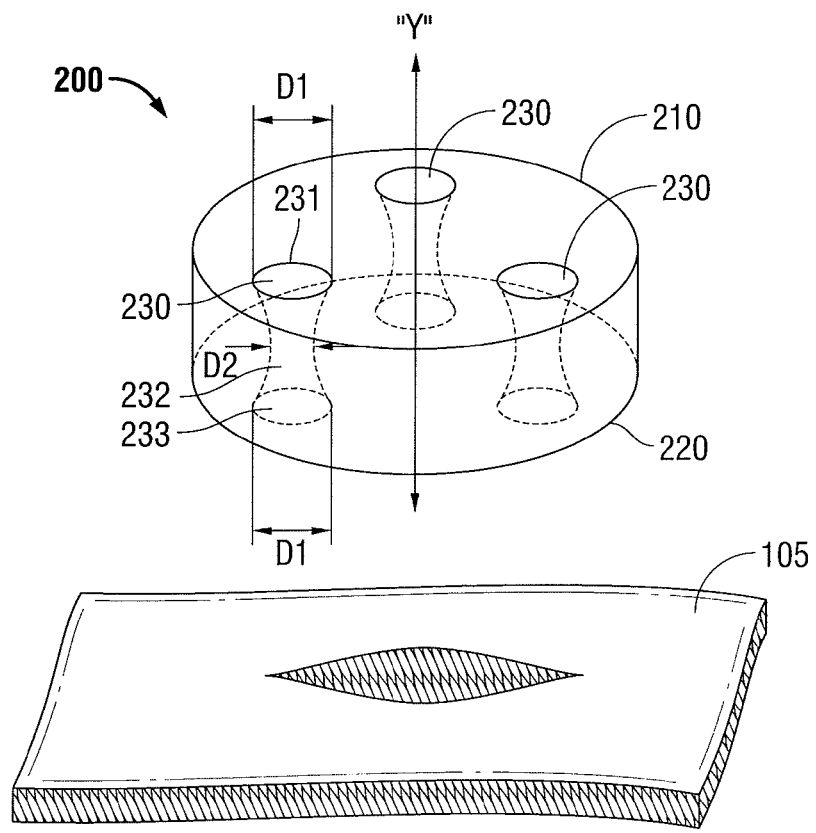
FIG. 5A is a perspective view of an alternate embodiment of the surgical apparatus of FIG. 1.
Figure 5B:
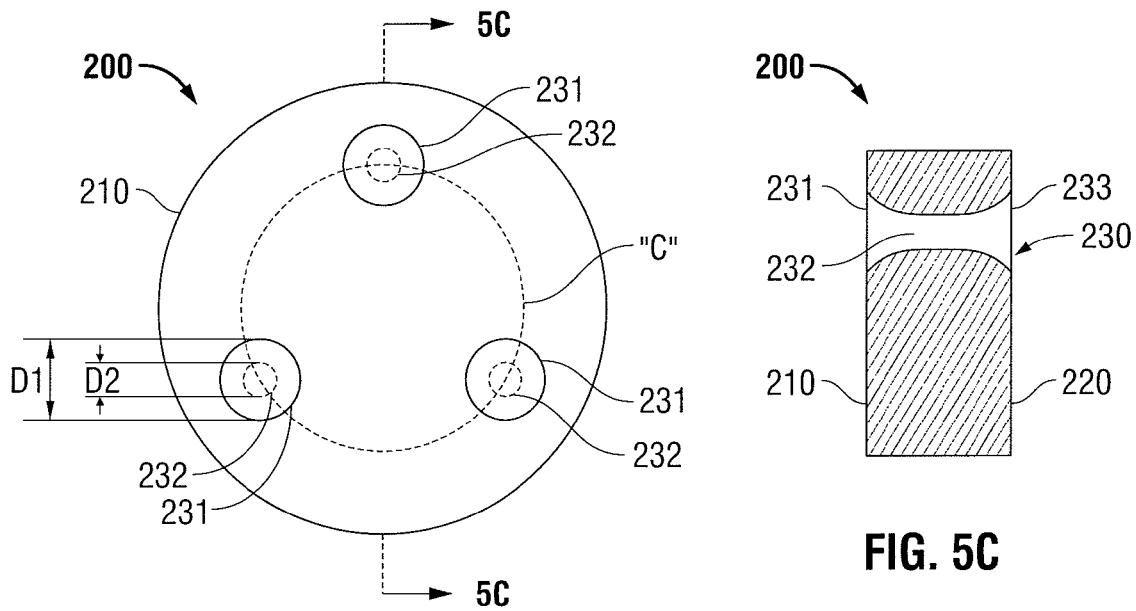
FIG. 5B is a top perspective view of the surgical apparatus of FIG. 5A.
Figure 5C:
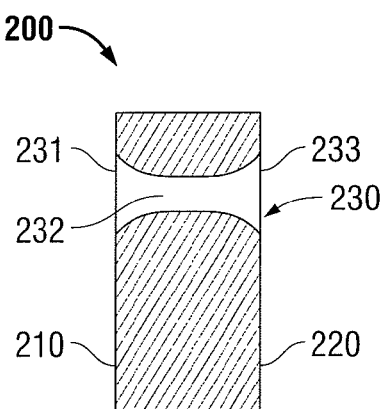
FIG. 5C is an end cross-sectional view of the surgical apparatus of FIG. 5B taken along the line 5C-5C.

FIGS. 5A-5C illustrates an alternate embodiment of the seal anchor member 200 in which the member 200 exhibits a disk-like configuration. The member 200 comprises at least one port 230 extending longitudinally along the longitudinal axis "Y" from the distal end 220 of the member 200 to the proximal end 210 thereof. Each port 230 defines a proximal opening 231 at the proximal end 210 of the member 200, a distal opening 233 at the distal end 220 of the member 200, and a passage from the proximal opening 231 to the distal opening 233. As shown in FIGS. 5A-5B, the member 200 may include three ports 230 which are positioned circumferentially on an imaginary circle "C" and are equidistant from each other. Alternatively, other arrangements of the ports 230 are envisioned, such as the distance between adjacent ports 230 may vary. In one embodiment, as illustrated in FIGS. 5A and 5C, each port 230 does not have a uniform diameter along its longitudinal length. Rather, each port 230 defines an hourglass configuration. Specifically, the end openings 231 and 233 define a radial diameter "D1" greater than the radial diameter "D2" defined by the middle portion 232 of the port 230. Simply stated, the port 230 has a gradually enlarging radial diameter starting from its middle portion 232 towards both end openings 231 and 233. The varying radial diameters of the port 230 along its longitudinal length allow the port 230 to sealingly engage instruments of varying diameters. For instance, the port openings 231 and 233 that define a large diameter "D1" is configured to form a seal about instruments of large diameters greater than or equal to "D1", whereas the middle portion 232 that defines a relatively small diameter "D2" is configured to sealingly engage instruments having diameters greater than or equal to "D2". The middle portion 232 is configured to expand to permit passage of the instrument upon insertion of the instrument, and is also configured to contract back to its original shape upon removal of the instrument. Further, the hourglass configuration of each port 230 facilitates easy insertion and removal of instruments through the end openings 231 and 233. The instrument does not experience a constant, uniform friction throughout the length of the port 230 during insertion or removal, as in the case with ports having a constant diameter along its length. Rather, for an instrument having a radial diameter greater than "D2" but less than "D1", the instrument experiences no friction due initial insertion into the large diameter "D1" of the proximal end opening 231 thereby reducing force required to insert the instrument as well as facilitating the insertion process. The instrument experiences a increasing friction as it approaches the middle portion 232 which forms a tight seal about the instrument. Upon removal of the instrument from the port 230, the instrument experiences a constantly decreasing friction as it passes the middle portion 232 exiting towards the proximal opening 231, thereby reducing force required to remove the instrument as well as facilitating the removal process. Hence, the surgical instrument experiences varying degrees of friction in this embodiment, as opposed to experiencing a constant uniform friction throughout the entire length of the ports with a constant diameter. In operation, introducing or removing the surgical instrument into or from the port of this embodiment requires less force and less time than that otherwise would require by using ports having a constant diameter.

FIG. 6A illustrates another embodiment of the seal anchor member 300, in which the member 300 comprises at least one port 330. In one embodiment, the member 300 comprises four ports 330. Similar to the embodiment illustrated in FIG. 5B, the four ports 330 are positioned circumferentially on an imaginary circle "C" and are equidistant from each other. Alternatively, other arrangements of the ports 330 are envisioned, such as the distance between adjacent ports 330 may vary. Similar to the port 230 described in FIGS. 5A-5C, the at least one port 330 has an hourglass configuration defining a large diameter "D1" at the end openings 331 and 333, and a small diameter "D2" at the middle portion 332. Unlike the configuration of the port 230, the at least one port 330 may be configured to have a membrane 334 placed somewhere along the longitudinal length thereof. For instance, in one embodiment as illustrated in FIG. 6B1, the membrane 334 is placed at the middle portion 332 of the port 330. In an alternate embodiment, the membrane 334 may be placed at either end opening 331 or 333 of the port 330 as illustrated in FIG. 6B2, where the member 334 is placed at the distal end opening 333. The membrane 334 has the same material property as the membrane 140 described earlier such that the membrane 334 can be easily penetrated therethrough by a sharp-pointed object. The closure of the membrane 334 inhibits the escape of the insufflation gas from the patient's peritoneal cavity and also functions to inhibit foreign matter from inadvertently entering the peritoneal cavity.

In alternate embodiments, the ports of the seal anchor member may not necessarily be placed on the circumference of the same imaginary circle "C". They may be spaced either a larger or smaller distance from the longitudinal axis "Y". The distance between adjacent ports may vary.

Moreover, features described in one embodiment may be combined with features described in other embodiments. For instance, a seal anchor member 100 with an hourglass configuration may comprise at least one port that has an hourglass configuration with a membrane placed somewhere along the length of the port. In another embodiment, a seal anchor member 200 with a disk-like configuration may comprise at least one port that has at least one lip defining a round apex and a round base. In another alternate embodiment, a seal anchor member 300 with a disk-like configuration may comprise three ports each of which defines an hourglass configuration with an open-through passage.

Accordingly, while several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical apparatus for positioning within a tissue tract accessing an underlying body cavity, which comprises:
    a seal anchor member comprising a leading end, a trailing end, and at least one longitudinal port defining a passage extending between the leading and trailing ends and being configured for reception of an object, the seal anchor member formed of a compressible material such that the seal anchor member is transitionable between an expanded state and a compressed state; and
    a membrane having a closed configuration and an open configuration, the membrane formed across the at least one longitudinal port in the closed configuration,
    wherein when the membrane is in the closed configuration, the membrane defines a gas impermeable barrier across the at least one longitudinal port, and
    wherein rupturing the membrane in the closed configuration irreversibly changes the membrane to the open configuration such that, in the absence of the object, gas is in communication across the membrane through the at least one longitudinal port between the leading and trailing ends of the seal anchor member.

2. The surgical apparatus of claim 1, wherein the membrane is monolithically formed with the at least one longitudinal port.

* * * * *